United States Patent [19]

Balding et al.

[11] Patent Number: 6,165,207
[45] Date of Patent: Dec. 26, 2000

[54] METHOD OF SELECTIVELY SHAPING HOLLOW FIBERS OF HEAT EXCHANGE CATHETER

[75] Inventors: David P. Balding, Mission Viejo; Steven Craig Foster, Orange, both of Calif.

[73] Assignee: Alsius Corporation

[21] Appl. No.: 09/321,515

[22] Filed: May 27, 1999

[51] Int. Cl.⁷ ...................................................... A61F 7/00
[52] U.S. Cl. ........................... 607/105; 606/22; 604/113; 428/399
[58] Field of Search .............................. 607/96, 104, 105, 607/113; 606/22, 27; 604/113; 428/398, 399, 364

[56] References Cited

U.S. PATENT DOCUMENTS

| | | |
|---|---|---|
| Re. 32,983 | 7/1989 | Levy . |
| Re. 33,561 | 3/1991 | Levy . |
| 2,058,780 | 10/1936 | Elliott . |
| 2,077,453 | 4/1937 | Albright . |
| 2,308,484 | 1/1943 | Auzin et al. . |
| 2,623,266 | 12/1952 | Hemmi . |
| 3,125,096 | 3/1964 | Antiles et al. . |
| 3,142,158 | 7/1964 | Podolsky . |
| 3,238,944 | 3/1966 | Hirschhorn . |
| 3,282,267 | 11/1966 | Eidus . |
| 3,327,713 | 6/1967 | Eidus . |
| 3,425,419 | 2/1969 | Dato . |
| 3,504,674 | 4/1970 | Swenson et al. . |
| 3,738,372 | 6/1973 | Shioshvili . |
| 3,776,241 | 12/1973 | Magilton et al. . |
| 3,897,790 | 8/1975 | Magilton et al. . |
| 3,913,581 | 10/1975 | Ritson et al. . |
| 4,010,795 | 3/1977 | Stenberg . |
| 4,111,209 | 9/1978 | Wolvek et al. . |
| 4,154,245 | 5/1979 | Daily . |
| 4,249,923 | 2/1981 | Walda . |
| 4,298,006 | 11/1981 | Parks . |
| 4,416,280 | 11/1983 | Carpenter et al. . |
| 4,416,281 | 11/1983 | Cooper et al. . |
| 4,583,969 | 4/1986 | Mortensen . |
| 4,672,962 | 6/1987 | Hershenson . |
| 4,745,922 | 5/1988 | Taylor . |
| 4,748,979 | 6/1988 | Hershenson . |
| 4,750,493 | 6/1988 | Brader . |
| 4,754,752 | 7/1988 | Ginsberg et al. . |
| 4,759,349 | 7/1988 | Betz et al. . |
| 4,791,930 | 12/1988 | Suzuki et al. . |
| 4,813,210 | 3/1989 | Masuda et al. . |
| 4,823,076 | 4/1989 | Haines et al. . |

(List continued on next page.)

FOREIGN PATENT DOCUMENTS

WO 98/26831 6/1998 WIPO .
WO 98/31312 7/1998 WIPO .

Primary Examiner—Linda C. M. Dvorak
Assistant Examiner—Roy Gibson

[57] ABSTRACT

A group of multiple hollow fibers may be shaped to introduce angular divergence among the fibers, or to introduce a selected longitudinal oscillation into the fibers. In one shaping technique, the fibers are held in parallel while upper and lower crimping assemblies of parallel crimping bars are drawn together on opposite sides of the parallel fibers. When bars of the opposing assemblies draw sufficiently close, they sandwich the fibers in between them, causing each fiber to assume a shape that oscillates as the fiber repeatedly goes over and then under successive bars. Since the crimping bars are aligned at oblique angles to the fibers, the peaks and troughs of successive fibers are offset. While in this position, the fibers are heated and then cooled to permanently retain their shapes. A different shaping technique utilizes a lattice of crisscrossing tines defining multiple apertures. In this technique, the lattice and fibers are positioned so that each fiber passes through one of the apertures. Then, the lattice and/or the fibers are slid apart or together until the lattice holds the fibers in a desired configuration, where the fibers have a prescribed outward divergence relative to each other. While in this position, the fibers are heated and then cooled to permanently retain this angular divergence.

30 Claims, 7 Drawing Sheets

U.S. PATENT DOCUMENTS

| | | |
|---|---|---|
| 4,844,074 | 7/1989 | Kurucz . |
| 4,850,958 | 7/1989 | Berry et al. . |
| 4,860,744 | 8/1989 | Johnson et al. . |
| 4,883,455 | 11/1989 | Leonard . |
| 4,899,741 | 2/1990 | Bentley et al. . |
| 4,920,963 | 5/1990 | Brader . |
| 4,940,617 | 7/1990 | Baurmeiater ........................ 428/36.3 |
| 4,941,475 | 7/1990 | Williams et al. . |
| 4,979,274 | 12/1990 | McCullough, Jr. et al. . |
| 4,987,896 | 1/1991 | Nakamatsu . |
| 5,019,075 | 5/1991 | Spears et al. . |
| 5,021,045 | 6/1991 | Buckberg et al. . |
| 5,041,089 | 8/1991 | Mueller et al. . |
| 5,066,578 | 11/1991 | Wikman-Coffelt . |
| 5,078,713 | 1/1992 | Varney . |
| 5,092,841 | 3/1992 | Spears . |
| 5,098,376 | 3/1992 | Berry et al. . |
| 5,106,360 | 4/1992 | Ishiwara et al. . |
| 5,139,496 | 8/1992 | Hed . |
| 5,147,355 | 9/1992 | Friedman et al. . |
| 5,147,385 | 9/1992 | Beck et al. . |
| 5,151,100 | 9/1992 | Abele et al. . |
| 5,158,534 | 10/1992 | Berry et al. . |
| 5,174,285 | 12/1992 | Fontenot . |
| 5,182,317 | 1/1993 | Winters et al. . |
| 5,191,883 | 3/1993 | Lennox et al. . |
| 5,196,024 | 3/1993 | Barath . |
| 5,211,631 | 5/1993 | Sheaff . |
| 5,230,862 | 7/1993 | Berry et al. . |
| 5,248,312 | 9/1993 | Langberg . |
| 5,250,070 | 10/1993 | Parodi . |
| 5,257,977 | 11/1993 | Eshel . |
| 5,261,399 | 11/1993 | Klatz et al. . |
| 5,262,451 | 11/1993 | Winters et al. . |
| 5,269,758 | 12/1993 | Taheri . |
| 5,275,595 | 1/1994 | Dobak, III . |
| 5,279,598 | 1/1994 | Sheaff . |
| 5,281,213 | 1/1994 | Milder et al. . |
| 5,281,215 | 1/1994 | Milder . |
| 5,324,286 | 6/1994 | Fowle . |
| 5,338,770 | 8/1994 | Winters et al. . |
| 5,342,301 | 8/1994 | Saab . |
| 5,342,693 | 8/1994 | Winters et al. . |
| 5,354,277 | 10/1994 | Guzman et al. . |
| 5,411,477 | 5/1995 | Saab . |
| 5,423,807 | 6/1995 | Milder . |
| 5,437,673 | 8/1995 | Baust et al. . |
| 5,450,516 | 9/1995 | Pasquali et al. ........................ 385/115 |
| 5,452,582 | 9/1995 | Longsworth . |
| 5,470,659 | 11/1995 | Baumgart et al. ...................... 428/398 |
| 5,478,309 | 12/1995 | Sweezer et al. . |
| 5,486,204 | 1/1996 | Clifton . |
| 5,486,208 | 1/1996 | Ginsberg . |
| 5,531,776 | 7/1996 | Ward et al. . |
| 5,545,161 | 8/1996 | Imran . |
| 5,562,606 | 10/1996 | Huybregts . |
| 5,609,620 | 3/1997 | Daily . |
| 5,624,392 | 4/1997 | Saab . |
| 5,655,548 | 8/1997 | Nelson et al. . |
| 5,656,420 | 8/1997 | Chien . |
| 5,693,080 | 12/1997 | Wallstén et al. . |
| 5,702,435 | 12/1997 | Maytal . |
| 5,716,386 | 2/1998 | Ward et al. . |
| 5,725,949 | 3/1998 | Pasquali et al. ........................ 428/364 |
| 5,733,319 | 3/1998 | Neilson et al. . |
| 5,735,809 | 4/1998 | Gorsuch . |
| 5,758,505 | 6/1998 | Dobak, III et al. . |
| 5,759,182 | 6/1998 | Varney et al. . |
| 5,787,715 | 8/1998 | Dobak, III et al. . |
| 5,837,003 | 11/1998 | Ginsberg . |
| 5,876,667 | 3/1999 | Gremel et al. ............................ 422/44 |

METHOD OF SELECTIVELY SHAPING HOLLOW FIBERS OF HEAT EXCHANGE CATHETER

BACKGROUND OF THE INVENTION

1. Field of the Invention

The present invention relates to catheters that utilize a bundle of many small fibers to conduct heat or materials exchange with a target area of the human body. More particularly, the invention concerns a catheter manufacturing process that selectively shapes a group of multiple hollow fibers to introduce angular divergence among the fibers or to introduce a selected longitudinal oscillation into the fibers.

2. Description of the Related Art

In warm blooded creatures, temperature regulation is one of the most important functions of the body. Despite the known importance of properly maintaining body temperature, scientists have discovered certain beneficial effects of artificially inducing a hypothermic state. For instance, cooling the body can help regulate vital functions during surgery by lowering the metabolism. With stroke, trauma, and other pathological conditions, hypothermia is believed to also reduce the permeability of the blood/brain barrier. Induced hypothermia is believed to additionally inhibit the release of damaging neurotransmitters, inhibit calcium mediated effects, inhibit brain edema, and lower intra cranial pressure. Regardless of the particular mechanism, the present invention understands that fevers degrade the outcomes for patients suffering from brain trauma or stroke, and moreover that hypothermia can improve the outcomes for such patients.

Hypothermia may be induced locally or systemically. With local hypothermia, physicians focus their cooling efforts on a particular organ, limb, anatomical system, or other region of the body. With systemic hypothermia, doctors universally lower body temperature without particular attention to any body part.

Under one technique for inducing systemic hypothermia, physicians cool the patient's entire body by packing it in ice. Although this technique has been used with some success, some physicians may find it cumbersome and particularly time consuming. Also, it is difficult to precisely control body temperature with ice packing. As a result, the patient's body temperature overshoots and undershoots the optimal temperature, requiring physicians to add or remove ice. Furthermore, there is some danger of injuring the skin, which is necessarily cooled more than any other body part.

In another approach to systemic hypothermia, the patient is covered with a cooling blanket, such as an inflatable air- or water-filled cushion. Beneficially, cooling blankets offer improved temperature control because physicians can precisely regulate the temperature of the inflation medium. Nonetheless, some delay is still inherent, first for a cooling element to change the temperature of the cooling medium, and then for the temperature adjusted cooling medium to cool the desired body part. This delay is even longer if the targeted body part is an internal organ, since the most effective cooling is only applied to the skin, and takes some time to successively cool deeper and deeper layers within the body.

The present invention recognizes that a better approach to inducing hypothermia is by circulating a cooling fluid through a cooling catheter placed inside a patient's body. The catheter may be inserted into veins, arteries, cavities, or other internal regions of the body. The present assignee has pioneered a number of different cooling catheters and techniques in this area. Several different examples are shown U.S. application Ser. No. 09/133,813, entitled "Indwelling Heat Exchange Catheter and Method of Using Same," filed on Aug. 3, 1998. Further examples are illustrated in U.S. application Ser. No. 09/294,080 entitled "Catheter With Multiple Heating/Cooling Fibers Employing Fiber Spreading Features," filed on Apr. 19, 1999. The foregoing applications are hereby incorporated into the present application by reference. These applications depict catheters where the tip region includes multiple hollow fibers. The fibers carry a coolant that is circulated through the catheter. The thin walls and substantial surface area of the fibers are conductive to the efficient transfer of heat from surrounding body fluids/tissue to the coolant, thereby cooling the patient.

Advantageously, cooling catheters are convenient to use, and enable doctors to accurately control the temperature of a targeted region. In this respect, cooling catheters constitute a significant advance. This invention addresses improvements related to such catheters.

SUMMARY OF THE INVENTION

Broadly, the present invention recognizes that wider spatial distribution of heat exchange fibers in a catheter increases the catheter's rate of heat exchange. The approach of this invention may also be applied in areas other than heat exchange, such as materials exchange (e.g., the exchange of oxygen or another gas with surrounding blood or other liquid).

To achieve wider fiber distribution, the present invention introduces techniques to selectively shape hollow fibers. Shaping may be performed to introduce divergence ("splay") among the fibers, or alternatively to introduce a selected longitudinal oscillation into the fibers. In one shaping technique, the fibers are held in parallel while opposing assemblies of parallel crimping bars are drawn together on opposite sides of the parallel fibers. When bars of the opposing assemblies draw sufficiently close, they sandwich the fibers in between them, causing each fiber to assume a shape that oscillates as it repeatedly goes over and then under successive bars. The crimping bars are alligned at oblique angles to the fibers; thus, the peaks and troughs of each fiber are offset from every other fiber. While in this position, the fibers are heated and then cooled to permanently establish their shapes. Or, shape irregularities can be introduced into the fibers during fabrication when the fibers are malleable by directing air or objects against the fibers.

A different shaping technique utilizes a lattice of criss-crossing tines defining multiple apertures. In this technique, the lattice and fibers are arranged so that each fiber passes through one of the apertures. Then, the lattice and/or the fibers are slidably repositioned until the lattice holds the fibers with a prescribed outward divergence relative to each other. While in this position, the fibers are heated and then cooled to permanently retain this shape.

In one embodiment, the invention may be implemented to provide a method to shape a group of hollow fibers. In a different embodiment, the invention may be implemented to provide an apparatus such as a group of hollow fibers formed with the foregoing method, or a catheter with such a group of fibers.

The invention affords its users with a number of distinct advantages. For example, in comparison with conventional multi-fiber catheters, catheters of this invention exchange heat or materials with improved efficiency because the fibers are more thoroughly separated from each other. Either by splaying fibers away from each other, or by creating fibers that oscillate with a staged phase delay, the invention encourages fiber spreading. This helps avoid the creation of a common boundary layer among several fibers, since the fibers are more likely to be spread apart. The invention also provides a number of other advantages and benefits, which should be apparent from the following description of the invention.

DETAILED DESCRIPTION

The nature, objectives, and advantages of the invention will become more apparent to those skilled in the art after considering the following detailed description in connection with the accompanying drawings. As mentioned above, the invention concerns techniques for selectively shaping hollow fibers designed to exchange heat or materials with body fluids/tissue. As examples, hollow fibers are discussed herein, even though the fiber shaping techniques of this invention are similarly applicable to solid fibers. These techniques may be applied to introduce divergence among fibers in a bundle as the fibers exit a common point of attachment, or alternatively to introduce a selected longitudinal oscillation into the fibers.

Fiber Splaying

Introduction

Figure 1:
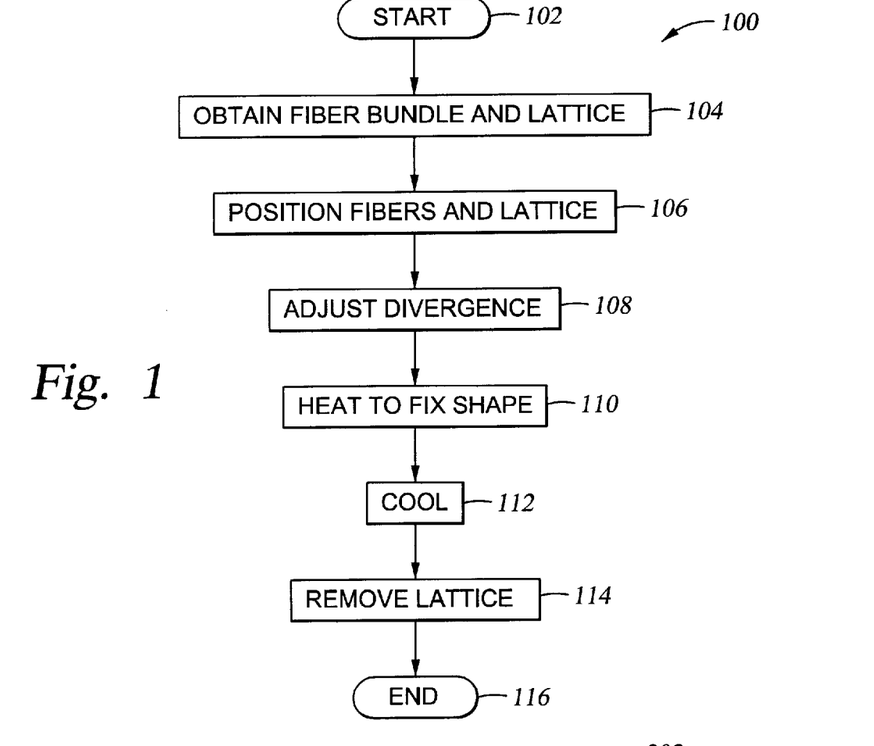
FIG. 1 is a flowchart of an operational sequence for selectively shaping a bundle of hollow fibers to introduce divergence among the fibers, in accordance with the invention.

FIG. 1 shows a sequence 100 to illustrate one example of the method aspect of the present invention. For ease of explanation, but without any intended limitation, the example of FIG. 1 is described in the context of various hardware components shown in FIGS. 2–6 and described below.

Obtaining Fiber Bundle

The sequence 100, which starts in step 102, describes a process of shaping fibers to introduce a prescribed divergence as the fibers exit from a common source of attachment. In step 104, a fiber bundle is obtained, which includes fibers stemming from a common attachment point at a distal end of a device such as a catheter 200, shown in FIG. 2. In this example, the fibers 202 proceed outward from a fluid transfer housing 204 located at the distal end of a catheter 200. The fibers 202 are collectively called a "bundle." Since they are not bound at their distal ends, the fibers are called "free tip."

Figure 2:
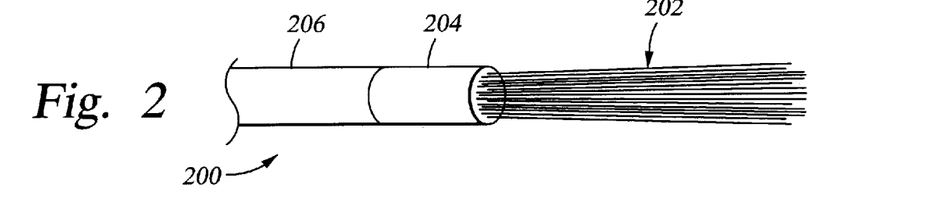
FIG. 2 is a perspective view of an exemplary fiber bundle according to this invention.

When the catheter is assembled, the housing 204 is coupled to a supply/return assembly 206 that includes supply and return conduits for circulating a fluid to/from the fibers 202. The supply/return assembly may comprise, for example, parallel or concentric fluid passageways. The housing 204 contains paths directing pre-circulation fluid from the supply conduit to the fibers, and other paths routing post-circulation fluid received from the fibers to the return conduit. In the example of FIG. 2, each fiber houses separate outward and inward fluid paths.

In one example, the fibers are non-porous and the fluid is a coolant such as water, saline, etc., used to cool blood, tissue, or other material that surrounds the catheter 200 while in use. In this embodiment, the entire catheter, including the fibers, is sealed to prevent any exchange of coolant with the body tissue or fluid surrounding the catheter. In another example, the catheter 200 contains oxygen, medicine, or another circulating substance that is distributed into surrounding blood, tissue, or other material surrounding the catheter 200 through tiny pores (not shown) in the fibers 202.

In contrast to the free tip fibers shown in FIG. 2, the invention may be applied to other fiber arrangements, such as fibers that are distally joined ("bound tip"), or fibers that individually proceed outward and return back to the fluid transfer housing ("looped fibers") to provide a unidirectional fluid path. Further details of catheters and fiber bundles are explained in the patent applications identified above and incorporated by reference.

Obtaining Lattice

Figure 3:
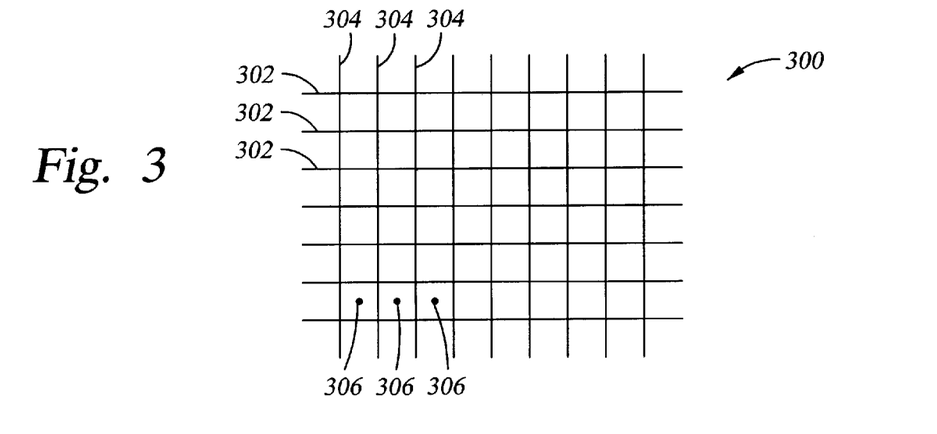
FIG. 3 is a plan view of an exemplary one-piece lattice, according to this invention.

In addition to the fiber bundle, step 104 also obtains a fiber positioning lattice. FIG. 3 shows an exemplary one-piece lattice 300. The lattice 300 is a planar structure that includes horizontal tines 302 and vertical tines 304 that criss-cross each other, forming apertures 306 between the tines 302, 304. In one example, the tines are spaced by approximately one millimeter, and comprise a non-abrasive material such as plastic, stainless steel, etc.

Figure 4:
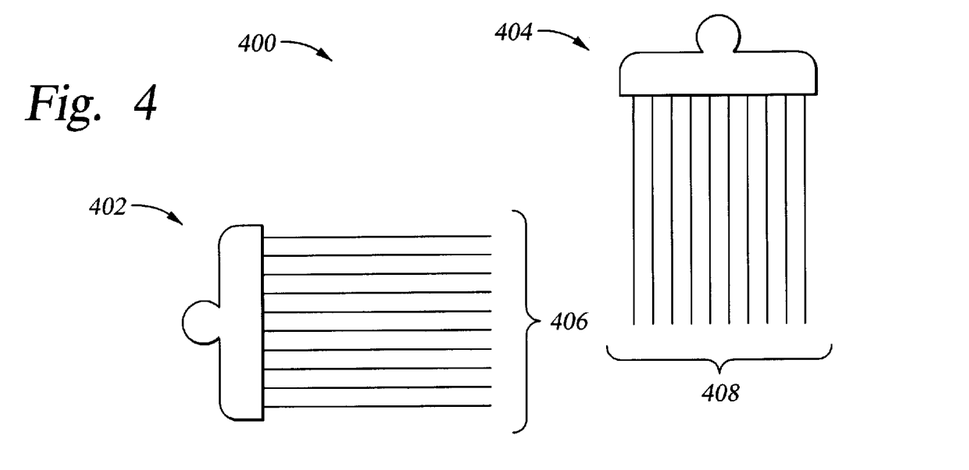
FIG. 4 is a plan view of an exemplary two-piece lattice, including first and second spacing assemblies, according to this invention.

As an alternative to the one-piece lattice 300 of FIG. 3, a multi-part lattice 400 may be used as shown in FIG. 4. The multi-part lattice is especially useful for bound tip fiber bundles or looped fibers. The lattice 400 includes first 402 and second 404 spacing assemblies. The spacing assemblies 402, 404 include respective sets of substantially parallel tines 406, 408, thereby forming comb-like shapes. The spacing assemblies 402, 404 may be slid together at right angles until they overlap and form a nearly planar structure like the lattice 300. In this overlapping configuration, the crisscrossing tines 406, 408 define apertures (not shown) such as those apertures 306 in the lattice 300.

Positioning Lattice and Fiber Bundle

After step 104, the fibers and desired lattice (300 or 400) are positioned such that each fiber passes through one of the lattice's apertures (step 106). In the case of the lattice 300, step 106 involves individually routing each fiber's distal end through one of the lattice apertures 306. In the case of the lattice 400, step 106 is performed by (1) sliding the spacing assembly 402 toward the fiber bundle so that free ends of the tines 406 pass into the fiber bundle 202 with individual fibers passing into the spaces between adjacent tines 406, and (2) sliding spacing assembly 404 into the fiber bundle 202 at a right angle to the spacing assembly 406. The assemblies 402, 404 may be brought together at another angle than perpendicular, however, recognizing that if the angle is too large or small the resultant apertures may be too long to hold the fibers in position.

Figure 5:
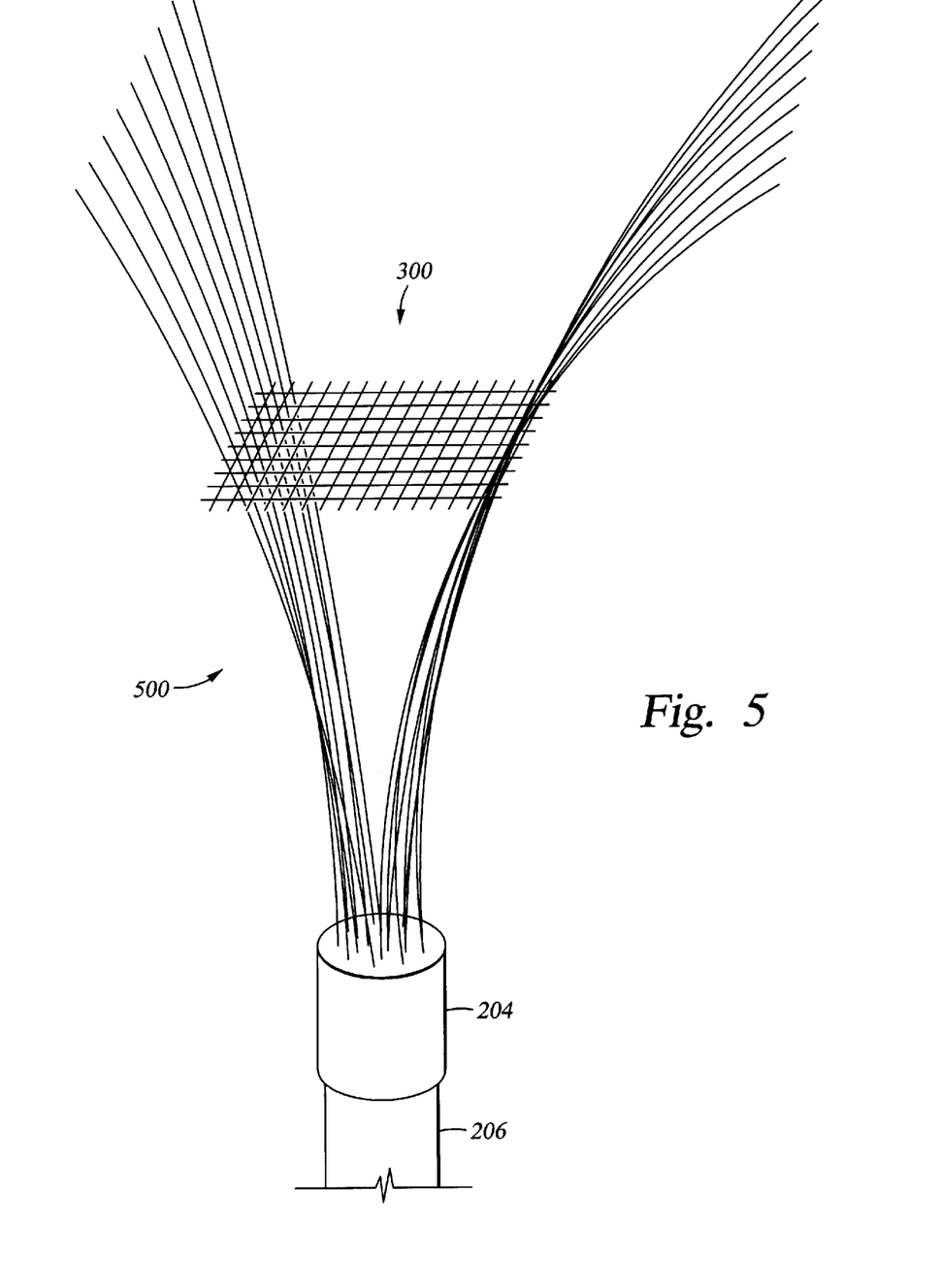
FIG. 5 is a perspective view of the fiber bundle of FIG. 1 with fibers held in position by the one-piece lattice of FIG. 3, in accordance with the invention.

FIG. 5 shows some fibers 500 after insertion into the lattice 300, after completion of step 106. The fibers 500 only represent some of the fibers 202, as the remaining fibers (which would appear in the middle of the lattice) are omitted from this drawing to enhance clarity and reduce clutter.

Adjusting Divergence

Figure 6:
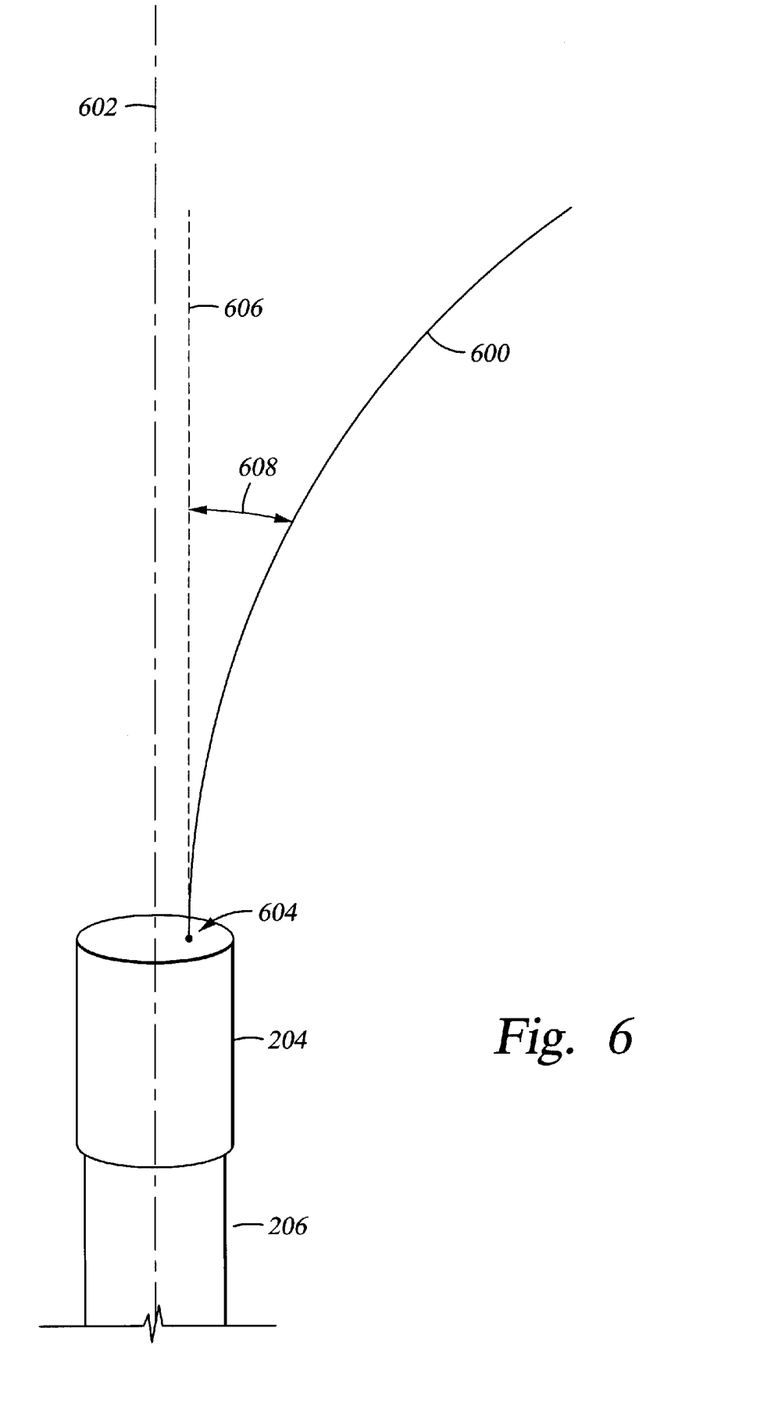
FIG. 6 is a perspective view of a partial fiber bundle to illustrate measurement of fiber splay, in accordance with the invention.

After step 106, step 108 is performed to adjust the divergence among the fibers, now routed through the lattice 300. FIG. 6 illustrates fiber divergence, also called "splay." Each fiber, such as the fiber 600, exits from the fluid transfer housing 204 at an exit point 604. Without any fiber divergence, the fibers would proceed outward from the housing 204 in a direction largely parallel to the longitudinal axis of the catheter 602. Namely, the fiber 600 would proceed outward from its exit point 604 along a line 606.

Step 108 adjusts fiber divergence by sliding the positioning lattice toward or away from the housing 204. When the lattice is moved toward the housing 204, the fiber 600 is bent outward from its normal path 606, increasing its divergence angle 608. Conversely, when the lattice is moved away from the housing 204, the fiber is not bent outward so much, decreasing its divergence angle 608. Consequently, step 108 involves sliding the lattice along the fibers (or vice versa) until the desired divergence angles are attained.

Heating & Cooling

At the conclusion of step 108, the fibers are held in their desired positions. To fix this position, the fibers (while held in place by the lattice) are heated to a prescribed temperature (step 110). This temperature is sufficiently high to reach a "fixing temperature" at which the fibers will retain their current shape even after the fibers cool. This varies according to the materials used. However, in the example of polyurethane fibers, step 110 may be performed using an oven to heat the fibers to about 180° F. for about one hour.

After step 110, step 112 cools the fibers. This may be achieved at a slower pace by permitting the structure to cool off at room temperature, or more quickly by immersing the fibers and their positioning lattice in a cool water bath. As an alternative to steps 110–112, the fiber shaping steps 106–108 may be performed during fiber fabrication, when the fibers are malleable.

Removing Lattice

After the fibers cool below their fixing temperature, the lattice is removed in step 114. Despite removal of the positioning lattice, the fibers retain their shape because of the heat fixing performed in step 110. After step 114, the fiber shaping is concluded and the routine 100 ends in step 116. Subsequent steps (not shown) are then performed to construct and assemble the remainder of the catheter.

Oblique Fiber Crimping

Introduction

Figure 7:
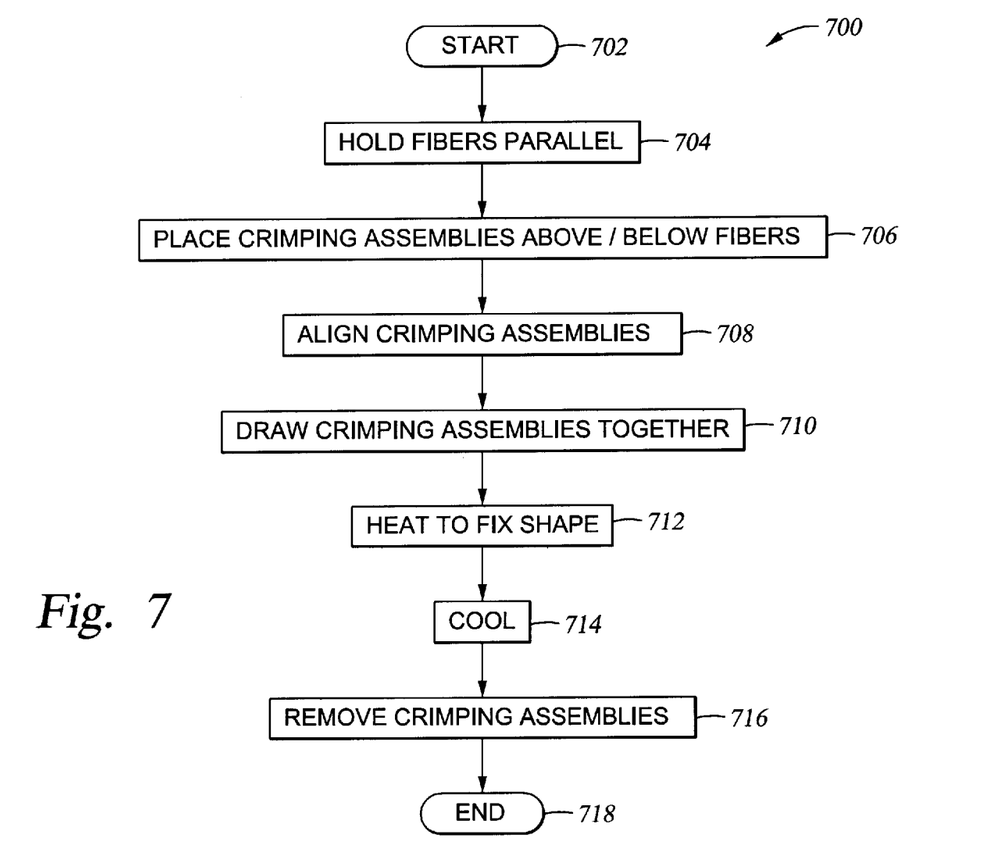
FIG. 7 is a flowchart of an operational sequence for selectively shaping a bundle of hollow fibers to introduce a selected longitudinal oscillation into the fibers.

FIG. 7 shows a sequence 700 to illustrate another example of the method aspect of the present invention. For ease of explanation, but without any intended limitation, the example of FIG. 7 is described in the context of the hardware components of FIGS. 8–11, as described below. The sequence 700, which starts in step 702, describes a process of shaping fibers to give the fibers a prescribed, periodic waviness. The fibers are placed side-by-side during shaping. From one fiber to the next, the peaks and troughs are successively delayed by a prescribed amount as a result of this procedure. Thus, the waveforms defined by the fibers are out of phase with each other. Alternatively, the waveforms may be irregular (i.e., non-periodic) if desired.

In the context of heat exchange catheters, the fibers comprise hollow, non-porous fibers such as polyurethane. In another example, the catheter may contain oxygen, a medicine, or another circulating substance that is exchanged with surrounding blood, tissue, or other material surrounding the catheter through tiny pores (not shown) in the fibers.

In step 704, retaining structures are used to hold the fibers in parallel. Although the fibers may already be mounted to a catheter prior to step 704, this step is more advantageously applied to unattached fibers, which are more conveniently laid in parallel with each other.

Figure 8:
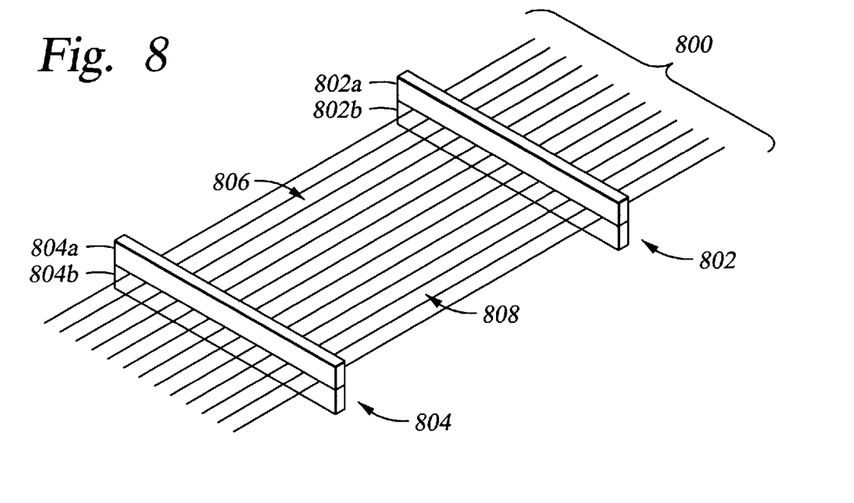
FIG. 8 is a perspective view of multiple fibers being held in position by a retainer, in accordance with the invention.

FIG. 8 shows one technique for holding fibers 800 in parallel, using retainers 802, 804. Each retainer 802, 804 is a two-piece assembly, having respective top members 802a, 804a and bottom members 802b, 804b. Top and bottom retaining members are held firmly together by structure discussed in greater detail below. In this configuration, the fibers 800 collectively form a ribbon shape having a top side 806 and a bottom side 808.

Figure 8A:
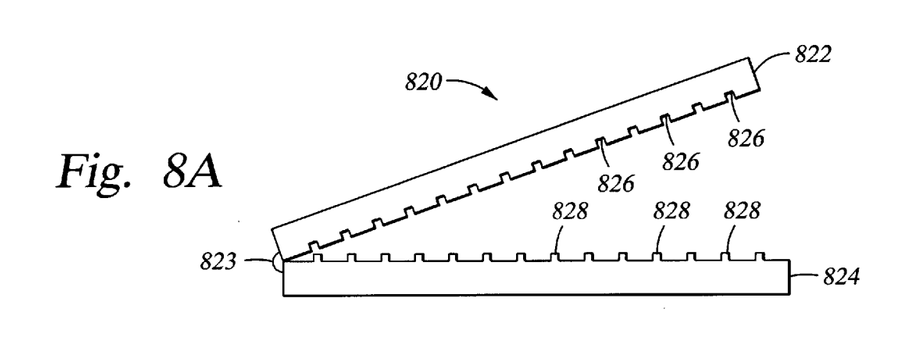
FIG. 8A is a plan view of an exemplary retainer, in accordance with the invention.
Figure 8B:
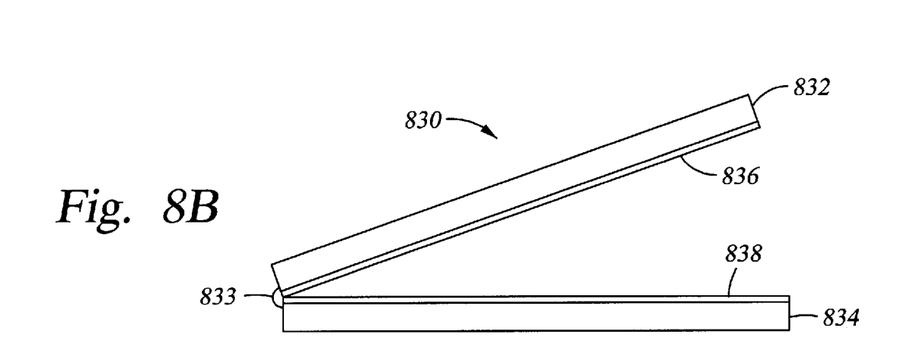
FIG. 8B is a plan view of a different retainer, in accordance with the invention.

FIGS. 8A–8B further illustrate some exemplary retainers. The retainer 820 (FIG. 8A) includes top and bottom members 822, 824 connected at a hinge 823. Opposite the hinge, the members 822, 824 may be clamped, bound, or otherwise fastened together to firmly hold fibers in between. The hinge 823 is merely one embodiment, and ordinarily skilled artisans (having the benefit of this disclosure) will recognize many other means for holding the top and bottom members 822, 824 together to sandwich the fibers in between.

The member 822 defines a series of grooves 826 to facilitate more convenient, even, and definitive distribution of fibers along the entire length of the retainer, with each fiber nestling into one groove. Opposite the grooves 826, the member 824 may optionally define a series of complementary teeth 828 to firmly hold each fiber in its respective groove.

The retainer 830 (FIG. 8B) also includes top and bottom members 832, 834. Though shown connected at a hinge 833, fastening of the members 832, 834 may be adapted in similar fashion as the retainer 820. Each member 832, 834 includes a supple gripping surface 836, 838, such as rubber, foam, or another firm but pliable substance for holding the fibers in place.

In addition to the embodiments 820, 830, ordinarily skilled artisans (halving the benefit of this disclosure) will understand that the invention further contemplates an extensive variety of non-disclosed retainers. One example is a hybrid combination (not is shown) of the retainers 820, 830, etc.

As another example (not shown), the proximal retainer may be constructed as shown above, with the distal retainer being a series of parallel posts. This embodiment is useful when each fiber comprises a loop that proceeds outward and loops back to its point of origination. The distal, looped ends of the fibers are retained by routing the fibers around respective posts of the distal retainer.

Placing Crimping Assemblies Above/Below Fibers

Figure 9:
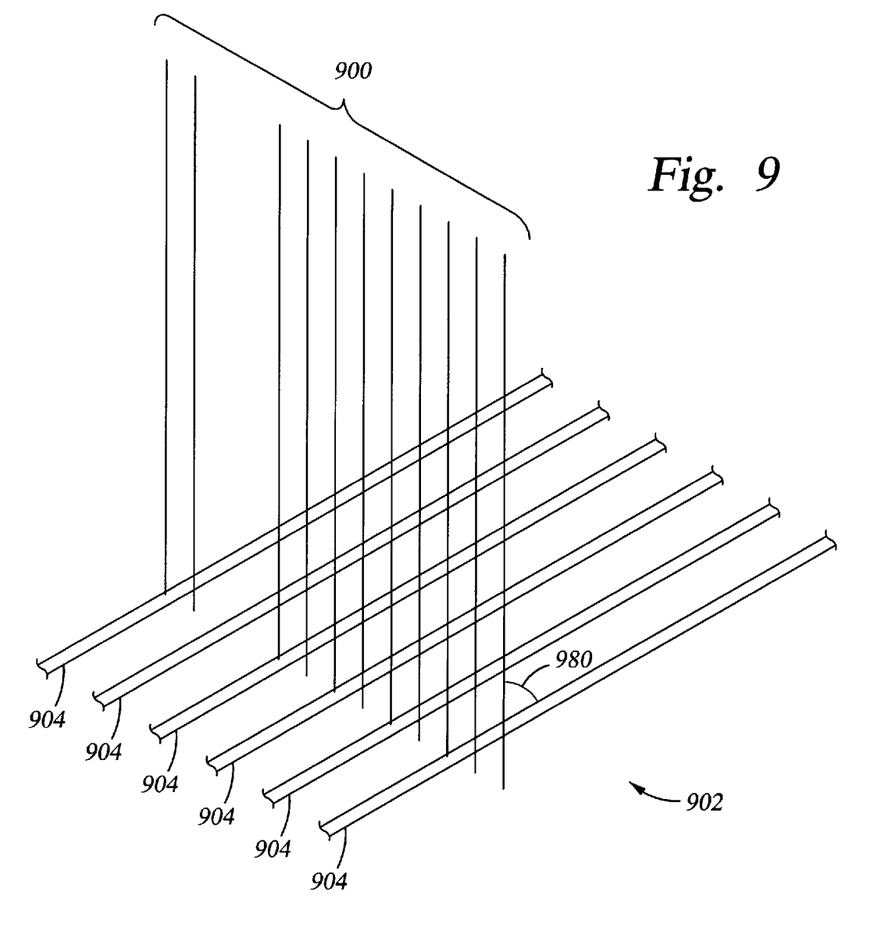
FIG. 9 is a perspective view of a top crimping assembly being aligned with fibers, in accordance with the invention.

With the retainers holding the fibers in parallel after step 704, step 706 then prepares for crimping of the fibers using crimping assemblies, the structure of which is discussed below. Namely, step 706 places one crimping assembly above the fibers, and one crimping assembly below the fibers. FIG. 9 shows an exemplary crimping assembly 902 above the fibers 900 (omitting the crimping assembly beneath the fibers 900, for clarity of illustration). The crimping assembly 902 above the fibers is referred to as an "upper" crimping assembly, whereas the other crimping assembly (not shown) is referred to as the "lower" crimping assembly. These terms are used merely for explanation and clarity of description, however, and terms such as "upper," "lower," and the like may be reversed without substantively changing their meaning.

Each crimping assembly includes a series of substantially parallel crimping bars, such as the bars 904 of the assembly 902. The size and spacing of the bars is selected depending upon factors such as the fiber diameter, fiber material, desired crimping pattern, etc. Although other arrangements may be used, the bars of the upper crimping assembly may be substantially equidistant, as with the bars of the lower crimping assembly. Furthermore, the distance between bars in the upper crimping assembly may be the same (or different) than the distance between bars in the lower crimping assembly, depending on the desired shape of post-crimping fibers.

The distance between adjacent crimping bars (measured center-to-center) defines the span between adjacent peaks and troughs in a fiber, i.e., one-half of the fiber's wavelength. The space between adjacent crimping bars is necessarily greater than the fiber diameter, to permit the fibers to run between the bars.

As am example, the crimping bars 904 may be mounted in position by a base member (not shown) secured to one end of each bar 904. One advantage of this single-base-member arrangement is that the crimping assemblies may be interleaved by positioning their base members toward the outside, with the bars' open ends coming together. Alternatively, two base members may be used for each crimping assembly, where one base member spans one end of the bars 904, and another base member spans the opposite end of the bars 904.

Figure 9A:
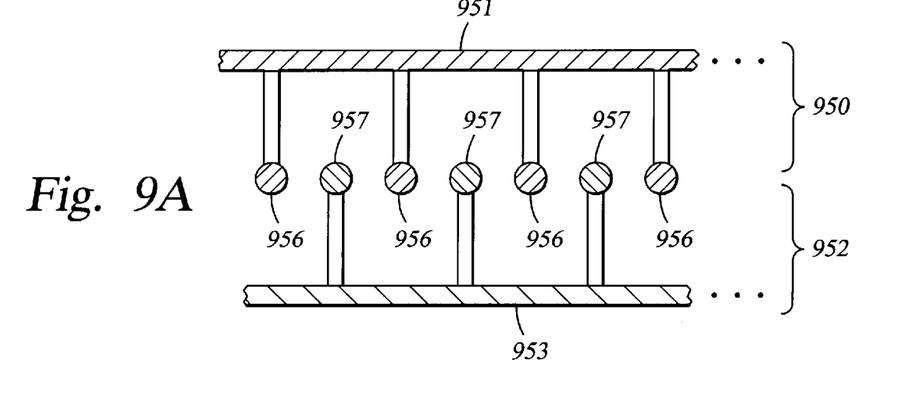
FIG. 9A is a cross-sectional side view of upper and lower crimping assemblies with offset base members to permit exaggerated crimping, in accordance with the invention.

FIG. 9A provides a cross-sectional depiction of a different example, which permits the bars of the two crimping assemblies to be brought together and actually past each other to cause a more drastic crimp. In this example, the bars of each crimping assembly are held in position by a base member that is offset from the axes of the bars. More particularly, the crimping assembly 950 includes bars 956 mounted to an offset base member 951; similarly, a crimping assembly 952 includes bars 957 mounted to an offset base member 953. With this arrangement, the bars 956, 957 may be brought into alignment with each other by urging the base members 951, 953 together; moreover, by continuing this motion one set of bars may actually be driven past the other set of bars to provide an exaggerated crimping configuration.

Aligning Crimping Assemblies

After step 706, the upper and lower crimping assemblies are aligned so that bars of the upper and lower assembly are substantially parallel to each other, and so that the parallel bars form an oblique angle to the parallel fibers. After crimping, the place where each bar contacts a fiber will provide a peak or trough in an oscillating pattern along the length of the fiber. Namely, the bars of one crimping assembly will define all fiber peaks, with the bars of the other crimping assembly defining all troughs (or vice versa). Step 708 reduces the likelihood that any two fibers reach their peaks and troughs at the same position along their lengths. This is the reason for the oblique alignment of bars with the fibers. To illustrate this in more detail, the bars are positioned so that the angle 980 (FIG. 9) formed with the fibers is neither 0°, 90°, 180°, nor 270°. In other words, the angles that the bars form with respect to the fibers are oblique, i.e., neither parallel nor perpendicular.

Equation 1 shows an exemplary computation of the angle 980.

$$\text{angle } 980 = \tan^{-1}(x \cdot n/\lambda) \qquad [1]$$

where:

x=the distance between adjacent fibers.

n=the number of fibers.

λ=the desired fiber wavelength, i.e., distance between successive peaks or troughs in one fiber.

Equation 1 computes the angle 980 such that, during the span of one fiber wavelength, all fibers successively reach their peak height, with none repeating. Ordinarily skilled artisans (having the benefit of this disclosure) will recognize a variety of other techniques for computing the angle 980, further description being unnecessary to the present disclosure.

Drawing Crimping Assemblies Together

Figure 10A:
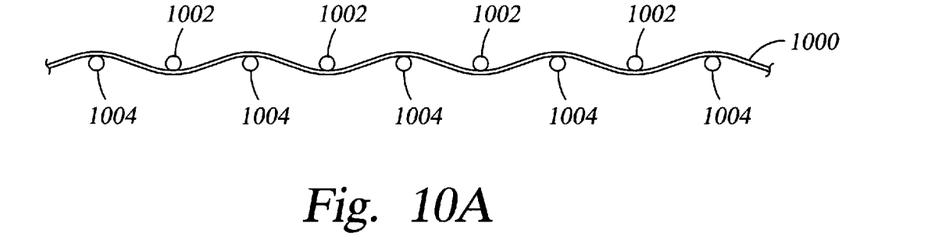
FIG. 10A is a cross-sectional side view of the crimping assemblies being drawn together, thereby sandwiching and crimping the intervening fibers, in accordance with the invention.
Figure 10B:
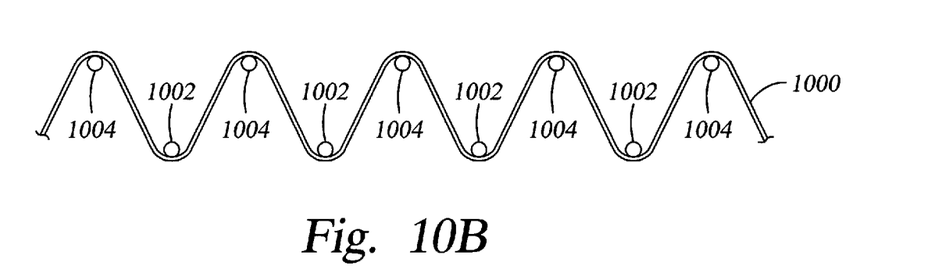
FIG. 10B is a cross-sectional side view of the crimping assemblies of FIG. 10A further drawn together to achieve exaggerated crimping, in accordance with the invention.

After the alignment of step 708, step 710 draws the upper and lower crimping assemblies together. The relative distance between the upper and lower crimping assemblies is reduced until the fibers bend into oscillating shapes that repeatedly curve back and forth longitudinally along the fibers, as the fibers pass around bars of the upper and lower assemblies in alternating fashion. FIG. 10A shows one example, where a fiber 1000 is being crimped between bars 1002 of an upper crimping assembly and bars 1004 of a lower crimping assembly. If desired, the crimping assemblies may be drawn past each other to achieve exaggerated crimping as shown in FIG. 10B.

If desired, step 710 may adjust tension on the fibers by changing the distance between the retainers (e.g., 802, 804 of FIG. 8) that hold the opposite ends of the fibers. Decreasing this distance releases strain on the fibers as the crimping assemblies re-route the fibers into a path that is longer then the straight distance between the fibers' ends due to the paths' repeated curves. Otherwise, without any narrowing of the retainers, the fibers may be excessively stretched or sheared while the crimping assemblies force the fibers to assume a longer, curving path. During step 710, the tension across the fibers may be selectively adjusted to form tighter crimps and a more triangular fiber oscillation (using more tension), or alternatively looser crimps with a more sinusoidal oscillation (using less tension).

Heating & Cooling

With the crimping assemblies sandwiching and effectively crimping the fibers as discussed in step 710, this configuration is held while the fibers are heated (step 712). The fibers are heated to a fixing temperature, causing the fibers to permanently maintain their crimped shape, despite subsequent cooling. This temperature varies according to the materials used. In the example of polyurethane fibers, step 712 may involve placing the fibers, retainers, and crimping assemblies into an oven and heating at 180° Fahrenheit for about one hour. After step 712, while still holding the fibers in their crimped position, the fibers are cooled (step 714). The fibers may be cooled by various techniques, such as removing them from the oven and letting them cool to room temperature, immersing the fibers in water or another cooling liquid, etc. During cooling, the fibers are still held in crimped form by the retainers and crimping assemblies to ensure that they cool beneath the fixing temperature while held in the desired position.

Removing Crimping Assemblies

After cooling, step 716 removes the crimping assemblies and retainers. Due to the heat shaping previously described, the fibers retain their crimped shape despite removal of the crimping assemblies. As a practical matter, the crimping assemblies may be removed earlier if desired, as long as the fibers have cooled sufficiently that they are no longer amenable to heat shaping.

Figure 11:
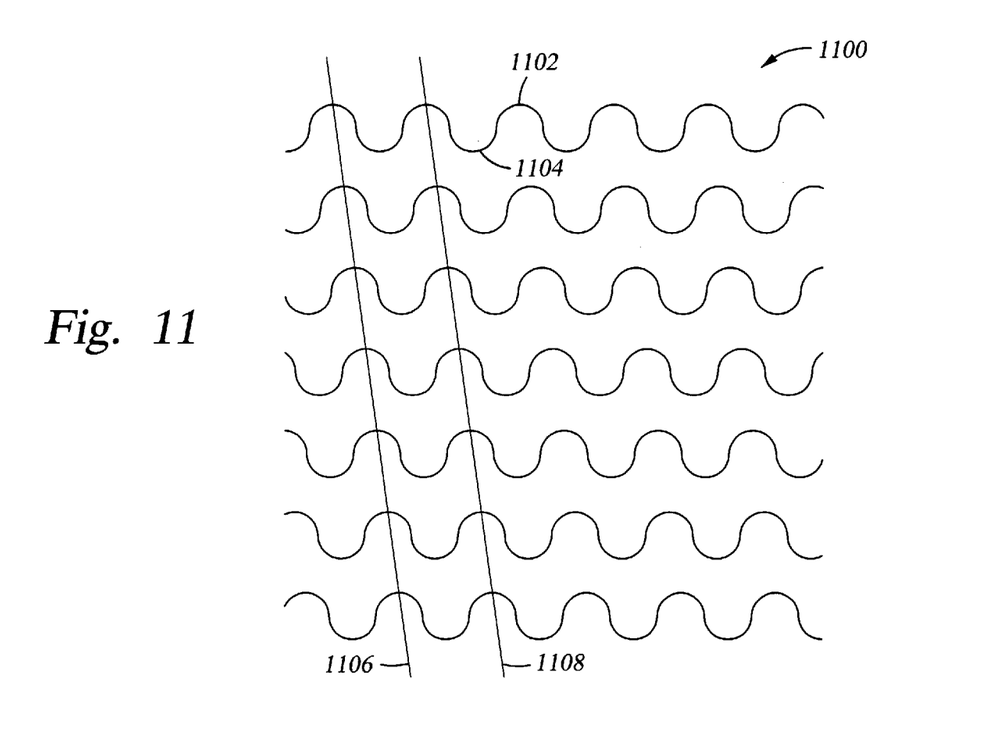
FIG. 11 is a plan view of the multiple fibers after undergoing oblique crimping according to the invention.

After completing the sequence 700, fibers remain crimped as shown by FIG. 11. Namely, each of the fibers 1100 oscillates sinusoidally along its length, presenting a series of troughs (such as 1104) and peaks (such as 1102). No two fibers reach a peak or trough at the same point. Instead, the fibers 1100 reach their peaks and troughs in successive order from the top of the page down, as viewed in FIG. 11. The fibers' peaks are aligned along lines such as the line 1106, the line 1108, etc.

OTHER EMBODIMENTS

While the foregoing disclosure shows a number of illustrative embodiments of the invention, it will be apparent to those skilled in the art that various changes and modifications can be made herein without departing from the scope of the invention as defined by the appended claims. For example, the present crimping fixture can be established by plural grooves, each describing a predetermined waveform different from the outer grooves, with fibers having mandrels inside being laid in the grooves and then heat treated as aggregate to cause the fibers to permanently assume the shapes of the respective grooves. Furthermore, although elements of the invention may be described or claimed in the singular, the plural is contemplated unless limitation to the singular is explicitly stated.

What is claimed is:

1. A method for shaping a group of multiple fibers, comprising the operations of:

holding the fibers substantially parallel to each other to form a plane defining top and bottom surfaces;

positioning an upper crimping assembly of substantially parallel crimping bars proximate the top surface;

positioning a lower crimping assembly of substantially parallel crimping bars proximate the bottom surface;

aligning the upper and lower crimping assemblies such that the bars are substantially parallel to each other, and the bars form an oblique angle to the fibers;

decreasing relative distance between the upper and lower crimping assemblies sufficient to bend the fibers into oscillating shapes that repeatedly curve back and forth longitudinally along the fibers as the fibers pass around bars of the upper and lower crimping assemblies in alternating fashion; and before or while the fibers are bent into the oscillating shapes, heating the fibers sufficiently for the fibers to adopt the oscillating shapes when cooled.

2. The method of claim 1, adjacent bars in the upper crimping assembly being substantially equidistant.

3. The method of claim 1, adjacent bars in the upper crimping assembly being separated by a first distance, and adjacent bars in the lower crimping assembly being separated by the first distance.

4. The method of claim 1, the holding operation releasing sufficient longitudinal tension on each fiber to permit bending of the fibers into substantially sinusoidal shapes.

5. The method of claim 1, the operation of decreasing relative distance moving at least one of the crimping assemblies such that the crimping assemblies proceed past each other.

6. The method of claim 5, the holding operation maintaining sufficient longitudinal tension on each fiber such that movement of the crimping assemblies past each other bends the fibers into oscillating triangular shapes.

7. A method for shaping a bundle of parallel fibers, the bundle having a proximal end where all fibers are joined, the method comprising the operations of:

providing a lattice of crisscrossing tines defining multiple apertures;

positioning the fibers and lattice such that each fiber passes through one of the apertures;

slidably adjusting the distance between the lattice and the bundle's proximal end until the lattice holds the fibers in a fixed configuration where the fibers have a prescribed outward divergence relative to each other; and before or while the fibers are held in the fixed configuration, heating the fibers sufficiently for the fibers to adopt the configuration when cooled.

8. The method of claim 7, the lattice being substantially planar.

9. The method of claim 7, where:

the lattice comprises separate upper and lower spacing assemblies each having multiple parallel tines separated by intervening spaces, the tines having base ends affixed to respective bases and also having free ends opposite the base ends;

the intersection of the spacing assemblies defines the apertures; and the positioning operation comprises: (a) sliding the free ends of the upper spacing assembly tines into the fiber bundle such that individual fibers pass into spaces between the upper spacing assembly's tines, and (b) sliding the free ends of the lower spacing assembly tines into the fiber bundle such that individual fibers pass into spaces between the spaces between the lower spacing assembly's tines.

10. The method of claim 9, where during the sliding of the free ends of the second spacing assembly tines, the second spacing assembly tines are substantially perpendicular to the first spacing assembly tines.

11. The method of claim 7, where:

the bundle has a distal end where the fibers are not joined;

the lattice comprises a substantially planar grid of tines; and the positioning operation comprises routing a distal end of each fiber through one of the apertures.

12. The method of claim 7, where the operation of slidably adjusting the distance between the lattice and the bundle's proximal end comprises sliding the lattice longitudinally along the fibers.

13. The method of claim 7, where the operation of slidably adjusting the distance between the lattice and the bundle's proximal end comprises sliding the fiber bundle toward or away from the lattice.

14. An apparatus comprising a group of multiple parallel fibers formed by a process comprising operations of:

holding the fibers substantially parallel to each other to form a plane defining top and bottom surfaces;

positioning an upper crimping assembly of substantially parallel crimping bars proximate the top surface;

positioning a lower crimping assembly of substantially parallel crimping bars proximate the bottom surface;

aligning the upper and lower crimping assemblies such that the bars are substantially parallel to each other, and the bars form an oblique angle to the fibers;

decreasing relative distance between the upper and lower crimping assemblies sufficient to bend the fibers into oscillating shapes that repeatedly curve back and forth longitudinally along the fibers as the fibers pass around bars of the upper and lower crimping assemblies in alternating fashion; and before or while the fibers are bent into the oscillating shapes, heating the fibers sufficiently for the fibers to adopt the oscillating shapes when cooled.

15. The apparatus of claim 14, adjacent bars in the upper crimping assembly being substantially equidistant.

16. The apparatus of claim 14, adjacent bars in the upper crimping assembly being separated by a first distance, and adjacent bars in the lower crimping assembly being separated by the first distance.

17. The apparatus of claim 14, the holding operation releasing sufficient longitudinal tension on each fiber to permit bending of the fibers into substantially sinusoidal shapes.

18. The apparatus of claim 14, the operation of decreasing relative distance moving at least one of the crimping assemblies such that the crimping assemblies proceed past each other.

19. The apparatus of claim 18, the holding operation maintaining sufficient longitudinal tension on each fiber such that movement of the crimping assemblies past each other bends the fibers into oscillating triangular shapes.

20. An apparatus comprising a bundle of parallel fibers formed by a process comprising operations of:

providing a lattice of crisscrossing tines defining multiple apertures;

positioning the fibers and lattice such that each fiber passes through one of the apertures;

slidably adjusting the distance between the lattice and the bundle's proximal end until the lattice holds the fibers in a fixed configuration where the fibers have a prescribed outward divergence relative to each other; and before or while the fibers are held in the fixed configuration, heating the fibers sufficiently for the fibers to adopt the configuration when cooled.

21. The apparatus of claim 20, the lattice being substantially planar.

22. The apparatus of claim 20, where:

the lattice comprises separate upper and lower spacing assemblies each having multiple parallel tines separated by intervening spaces, the tines having base ends affixed to respective bases and also having free ends free ends opposite the base ends;

the intersection of the spacing assemblies defines the apertures; and the positioning operation comprises: (a) sliding the free ends of the upper spacing assembly tines into the fiber bundle such that individual fibers pass into spaces between the upper spacing assembly's tines, and (b) sliding the free ends of the lower spacing assembly tines into the fiber bundle such that individual fibers pass into spaces between the spaces between the lower spacing assembly's tines.

23. The apparatus of claim 22, where during the sliding of the free ends of the second spacing assembly tines, the second spacing assembly tines are substantially perpendicular to the first spacing assembly tines.

24. The apparatus of claim 20, where:

the bundle has a distal end where the fibers are not joined;

the lattice comprises a substantially planar grid of tines; and the positioning operation comprises routing a distal end of each fiber through one of the apertures.

25. The apparatus of claim 20, where the operation of slidably adjusting the distance between the lattice and the bundle's proximal end comprises sliding the lattice longitudinally along the fibers.

26. The apparatus of claim 20, where the operation of slidably adjusting the distance between the lattice and the bundle's proximal end comprises sliding the fiber bundle toward or away from the lattice.

27. A catheter comprising:

a supply/return assembly;

multiple hollow fibers; and a fluid transfer housing mounted to a distal end of the supply/return assembly, and also connected to the fibers, the housing including outgoing and incoming fluid paths between the supply/return assembly and the fibers;

where the fibers have oscillating shapes that repeatedly curve back and forth along the fibers, each fibers' oscillations defining peaks and troughs longitudinally occurring along the fibers' length, and wherein a peak of at least one fiber is longitudinally offset from a peak of at one other fiber.

28. The catheter of claim 27, the oscillating shapes comprising sinusoidal shapes.

29. The catheter of claim 27, where the peaks of each fiber are longitudinally offset from the peaks of every other fiber.

30. A method for making a heat exchange catheter, comprising:

directing air or objects against plural hollow fibers while the fibers are in a malleable state; and arranging the fibers on a hollow catheter body in communication with at least one lumen of the body to establish a heat exchange catheter.

* * * * *